(12) United States Patent
Goble

(10) Patent No.: US 7,862,564 B2
(45) Date of Patent: Jan. 4, 2011

(54) METHOD OF REMODELLING STRETCH MARKS

(75) Inventor: Nigel M. Goble, Berkshire (GB)

(73) Assignee: Plasmogen Inc., New York, NY (US)

( * ) Notice: Subject to any disclaimer, the term of this patent is extended or adjusted under 35 U.S.C. 154(b) by 1100 days.

(21) Appl. No.: 11/589,908

(22) Filed: Oct. 31, 2006

(65) Prior Publication Data

US 2007/0073287 A1 Mar. 29, 2007

Related U.S. Application Data

(63) Continuation-in-part of application No. 10/792,765, filed on Mar. 5, 2004, now Pat. No. 7,335,199, which is a continuation-in-part of application No. 09/789,550, filed on Feb. 22, 2001, now Pat. No. 6,723,091.

(60) Provisional application No. 60/183,785, filed on Feb. 22, 2000.

(30) Foreign Application Priority Data

Sep. 25, 2006 (GB) ................................. 0618901.3

(51) Int. Cl.
 *A61B 18/14* (2006.01)
(52) U.S. Cl. .............................. 606/41; 606/40; 606/49; 607/96
(58) Field of Classification Search ............. 606/38–42, 606/45–50; 607/88–105
See application file for complete search history.

(56) References Cited

U.S. PATENT DOCUMENTS

| 2,909,735 | A | 10/1959 | Hessler, Jr. |
| 3,280,362 | A | 10/1966 | Ohtomo |
| 3,699,967 | A | 10/1972 | Anderson |
| 3,838,242 | A | 9/1974 | Goucher |
| 3,903,891 | A | 9/1975 | Brayshaw |

(Continued)

FOREIGN PATENT DOCUMENTS

DE 35 21 616 A1 12/1986

(Continued)

OTHER PUBLICATIONS

Pelah I. et al., "Differential calorimeter for measurement of absorbed energy in laser-produced plasmas", Review of Scientific Instruments USA, vol. 48, No. 8, Aug. 1977, pp. 1068-1071.

(Continued)

*Primary Examiner*—Michael Peffley
(74) *Attorney, Agent, or Firm*—Oliff & Berridge, PLC

(57) ABSTRACT

A cosmetic method of regenerating the skin in the region of a stretch mark is disclosed. The method comprises operating a source of thermal energy with a low thermal time constant, and directing it at the surface of the skin adjacent to and within a stretch mark forming first and second adjacent regions of thermally-modified tissue. The first region is adjacent to, and overlies, the second region, and the first region is thermally modified to a greater extend than the second region such that, following treatment, the width of the stretch mark is reduced and the reticular architecture of the dermis in the stretch mark is at least partially restored.

16 Claims, 8 Drawing Sheets

U.S. PATENT DOCUMENTS

| | | | |
|---|---|---|---|
| 4,040,426 A | | 8/1977 | Morrison, Jr. |
| 4,781,175 A | | 11/1988 | McGreevy et al. |
| 4,839,492 A | | 6/1989 | Bouchier et al. |
| 4,901,719 A | | 2/1990 | Trenconsky et al. |
| RE34,780 E | | 11/1994 | Trenconsky et al. |
| 5,364,392 A | | 11/1994 | Warner et al. |
| 5,458,596 A | * | 10/1995 | Lax et al. .................. 606/31 |
| 5,669,904 A | | 9/1997 | Platt, Jr. et al. |
| 5,669,907 A | | 9/1997 | Platt, Jr. et al. |
| 5,697,281 A | | 12/1997 | Eggers et al. |
| 5,720,745 A | | 2/1998 | Farin et al. |
| 5,742,718 A | | 4/1998 | Harman et al. |
| 5,755,753 A | | 5/1998 | Knowlton |
| 5,843,019 A | | 12/1998 | Eggers et al. |
| 5,843,078 A | * | 12/1998 | Sharkey .................. 606/41 |
| 5,888,198 A | | 3/1999 | Eggers et al. |
| 5,948,011 A | | 9/1999 | Knowlton |
| 5,968,034 A | | 10/1999 | Fullmer et al. |
| 6,024,733 A | | 2/2000 | Eggers et al. |
| 6,053,172 A | | 4/2000 | Hovda et al. |
| 6,063,084 A | | 5/2000 | Farin |
| 6,099,523 A | | 8/2000 | Kim et al. |
| 6,117,109 A | * | 9/2000 | Eggers et al. .............. 604/114 |
| 6,135,998 A | | 10/2000 | Palanker |
| 6,149,620 A | | 11/2000 | Baker et al. |
| 6,159,194 A | | 12/2000 | Eggers et al. |
| 6,190,381 B1 | | 2/2001 | Olsen et al. |
| 6,210,402 B1 | | 4/2001 | Olsen et al. |
| 6,213,999 B1 | | 4/2001 | Platt, Jr. et al. |
| 6,228,078 B1 | | 5/2001 | Eggers et al. |
| 6,296,636 B1 | | 10/2001 | Cheng et al. |
| 6,309,387 B1 | | 10/2001 | Eggers et al. |
| 6,334,074 B1 | * | 12/2001 | Spertell .................. 607/101 |
| 6,387,092 B1 | | 5/2002 | Burnside et al. |
| 6,413,253 B1 | | 7/2002 | Koop et al. |
| 6,443,948 B1 | | 9/2002 | Suslov |
| 6,464,681 B1 | | 10/2002 | Heuser |
| 6,475,215 B1 | | 11/2002 | Tanrisever |
| 6,518,538 B2 | | 2/2003 | Bernabei |
| 6,565,558 B1 | | 5/2003 | Lindenmeier et al. |
| 6,582,427 B1 | | 6/2003 | Goble et al. |
| 6,629,974 B2 | | 10/2003 | Penny et al. |
| 6,666,865 B2 | | 12/2003 | Platt |
| 6,723,091 B2 | | 4/2004 | Goble et al. |
| 6,920,312 B1 | | 7/2005 | Benjamin |
| 7,022,121 B2 | * | 4/2006 | Stern et al. .................. 606/41 |
| 2001/0034519 A1 | | 10/2001 | Goble et al. |
| 2002/0043520 A1 | | 4/2002 | Bernabei |
| 2002/0161362 A1 | | 10/2002 | Penny et al. |
| 2003/0069576 A1 | | 4/2003 | Tanrisever |
| 2003/0125727 A1 | | 7/2003 | Truckai |
| 2004/0044342 A1 | | 3/2004 | Mackay |
| 2004/0147985 A1 | | 7/2004 | MacFarland et al. |
| 2004/0186470 A1 | | 9/2004 | Goble et al. |
| 2005/0149012 A1 | | 7/2005 | Penny et al. |
| 2005/0256519 A1 | | 11/2005 | Goble et al. |
| 2006/0116674 A1 | | 6/2006 | Goble et al. |

FOREIGN PATENT DOCUMENTS

| | | |
|---|---|---|
| EP | 0 353 178 | 1/1990 |
| EP | 0 680 771 A1 | 11/1995 |
| EP | 0 787 465 A1 | 8/1997 |
| FR | 2 699 785 | 6/1994 |
| GB | 2 423 254 A | 8/2006 |
| JP | 09-299379 A2 | 11/1997 |
| JP | 09-299380 A2 | 11/1997 |
| JP | 10-024048 A2 | 1/1998 |
| JP | 10-024050 A2 | 1/1998 |
| JP | 10-286316 A2 | 10/1998 |
| RU | 2138213 C1 | 9/1999 |
| WO | WO 89/07921 | 9/1989 |
| WO | WO 95/00759 | 1/1995 |
| WO | WO 95/24111 | 9/1995 |
| WO | WO 95/26686 | 10/1995 |
| WO | WO 96/34568 | 11/1996 |
| WO | WO 98/35618 | 8/1998 |
| WO | WO 00/32127 | 6/2000 |
| WO | WO 00/53112 | 9/2000 |
| WO | WO 0162169 | 8/2001 |
| WO | WO 02/094116 A1 | 11/2002 |

OTHER PUBLICATIONS

Kulik P. et al., "Method for Measurement of Thermal-Flux Distribution in Low-Temperature Plasma", Instruments and Experimental Techniques, Consultants Bureau, New York, vol. 31, No. 2, Part 2, Mar. 1, 1988, pp. 410-412.

* cited by examiner

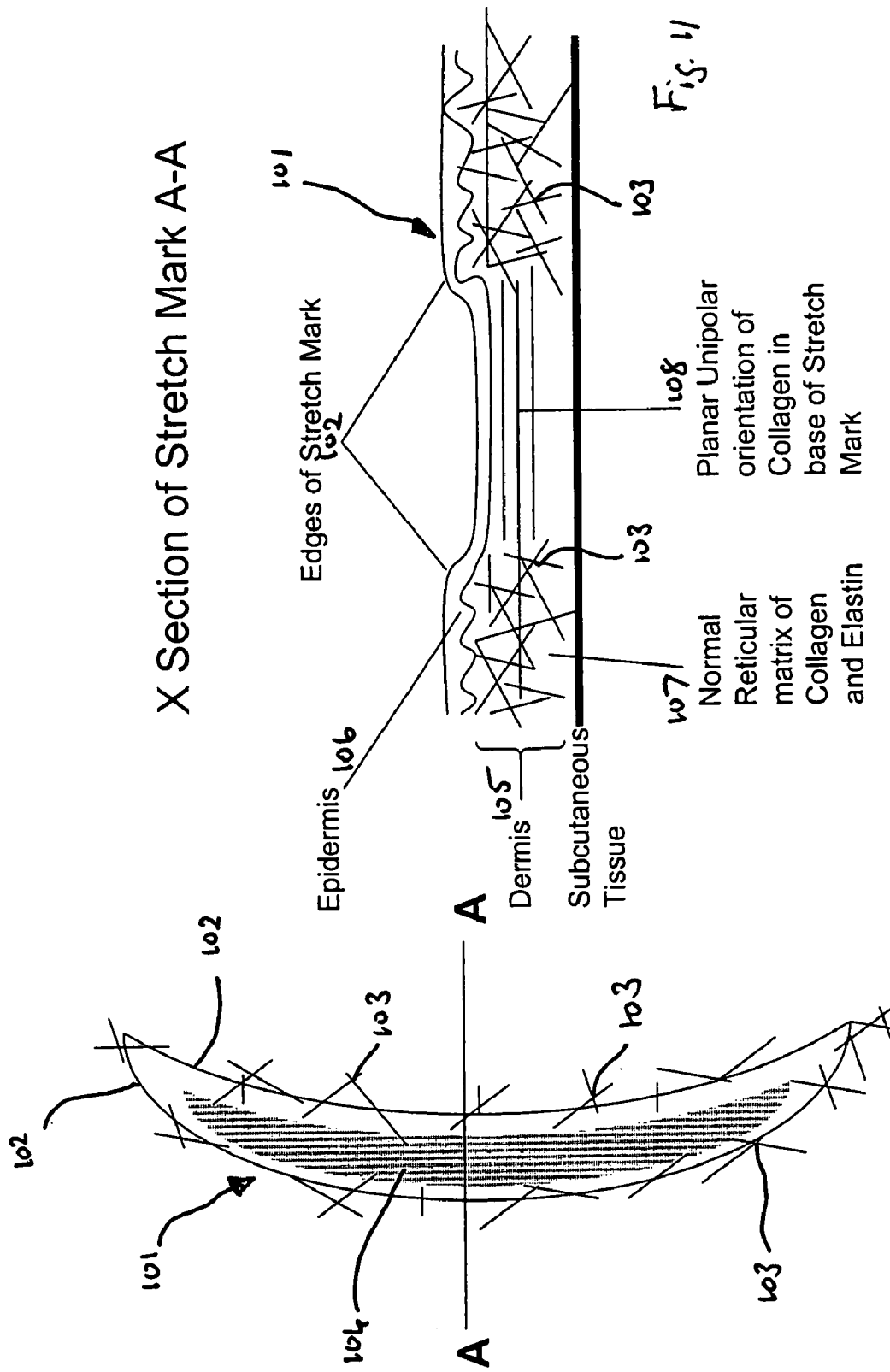

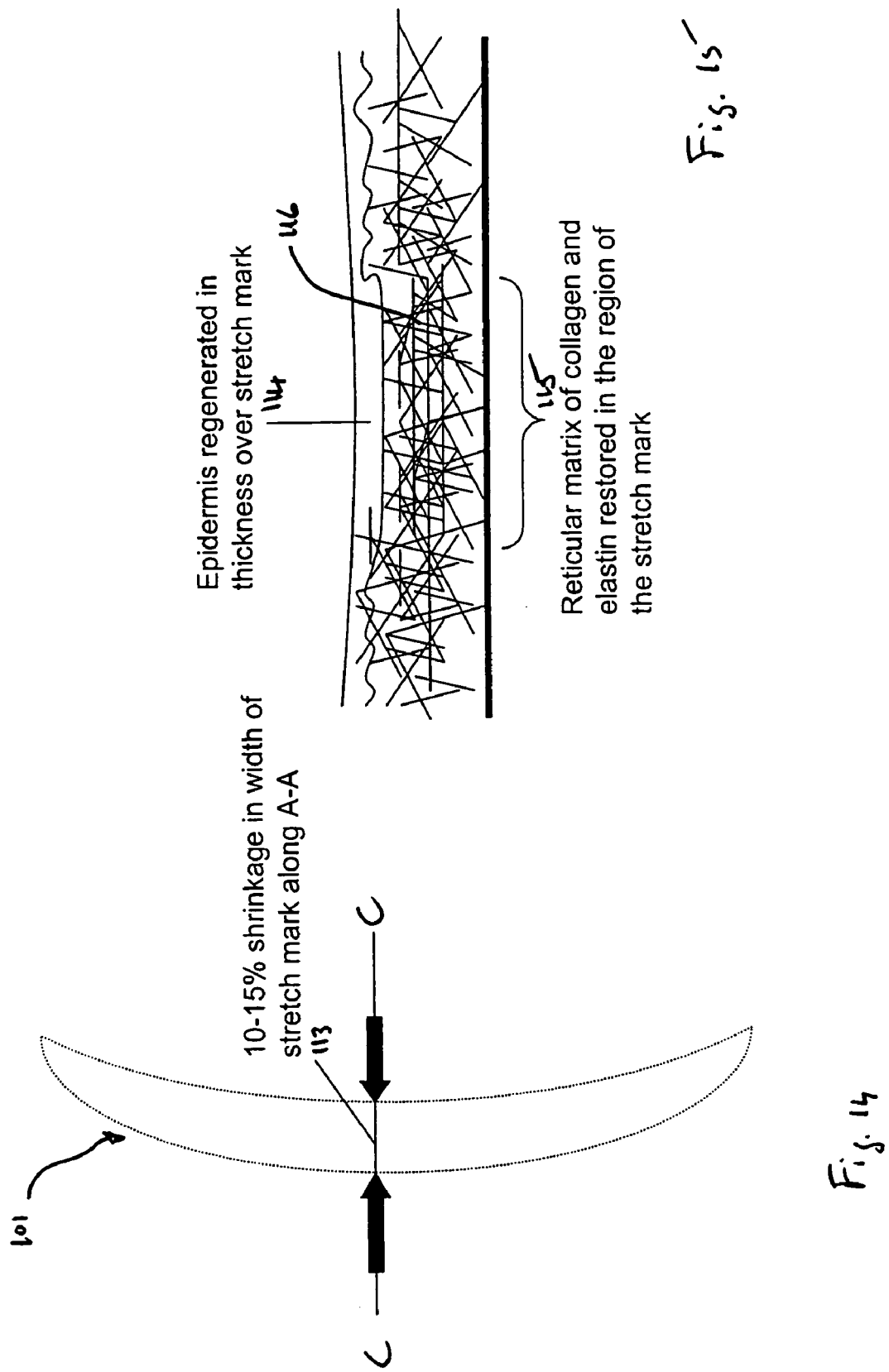

METHOD OF REMODELLING STRETCH MARKS

This is a Continuation-in-Part of U.S. patent application Ser. No. 10/792,765, filed Mar. 5, 2004, now U.S. Pat. No. 7,335,199, issued Feb. 26, 2008, that is a Continuation-in-Part Application of U.S. patent application Ser. No. 09/789,550, filed Feb. 22, 2001, now U.S. Pat. No. 6,723,091, issued Apr. 24, 2004, that in turn claims the benefit of priority of U.S. Provisional Patent Application No. 60/183,785, filed Feb. 22, 2000. The complete disclosure of each application, including the specifications, drawings, and claims are incorporated herein by reference in their entirety.

This invention relates to a method of collagen remodelling, and in particular to a method of remodelling defects of the skin known as a stretch marks.

Human skin has two principal layers: the epidermis, which is the outer layer and typically has a thickness of around 120 μm in the region of the face, and the dermis which is typically 20-30 times thicker than the epidermis, and contains hair follicles, sebaceous glands, nerve endings and fine blood capillaries. By volume the dermis is made up predominantly of the protein collagen, the fibres of which being arranged in a matrix pattern interspersed with finer less prevalent elastin and fibrillin fibres.

In association with a pubertal growth spurt, the increasing problem of obesity, the wearing of tight clothing, or as a result of hormone changes combined with the volumetric effects of a gravid uterus on the abdominal skin, the skin may be stretched to a degree that induces a defect known as a stretch mark or when associated with pregnancy striae gravidarum.

As the skin is stretched beyond its elastic point, it thins and the matrix orientation of collagen fibres becomes replaced with a horizontal unipolar orientation running across the width of the stretch mark. The thinning may be such that the stretch mark appears blue, due to the appearance of subcutaneous connective tissue below the dermis with the overlying epidermis having a shiny atrophic appearance. The edges of the stretch mark often have a cross-hatch pattern denoting the boundary between normal dermis and the dermis of the stretch mark in the area where the disruption of the normal reticular architecture of the dermis occurred. When associated with pregnancy or other hormonal changes, the skin of a stretch mark may exhibit excessive pigmentation, appearing darker than the adjacent normal skin.

Plasma Skin Regeneration (PSR) is technique employing an invention disclosed in U.S. patent applications Ser. Nos. 09/789,550, 10/073,179, 10/792,765 and 11/281,594. The method of treating the skin using PSR involves exposing the skin to pulses of nitrogen or other diatomic gas that has been ionised or otherwise elevated to an excited state using ultra-high frequency radiofrequency energy. The ionised gas stores energy that is given up to the skin as thermal energy, producing a heating of both the epidermis and the deeper dermis of the skin. The depth of the effect is a function of the power setting and the moisture content of the skin, provided the distance and the angle of the plasma pulse remains constant with respect to the skin surface.

The thermal effect on dermal collagen produces a denaturation of the dermal collagen. This denaturation process is known to be temperature and time dependent. It is also known that the birefringence of collagen fibres typically disappears on exposure of the collagen to a temperature more than 70-75° C.

Denaturation of collagen is also associated with a shortening of the collagen fibres, and this feature has been used to treat various collagen-containing structures of the body that have become stretched due to age or trauma. Examples known in the art include the thermal treatment of joint capsules, such as that of the shoulder, that have become stretched due to dislocation known as thermally-induced capsular shift, or the thermal treatment of the pelvic support ligaments of the urinary bladder to correct the anatomy and restore urinary continence.

In the healing process following treatment, the denatured collagen acts as a matrix into which new collagen grows as it is regenerated by fibroblasts. As described in U.S. patent application 60/053498, this can be used to treat photodamaged skin in which the dermal collagen and the elastin fibres have become deranged by UV exposure.

An aim of the invention is to apply thermal energy from a source with a low thermal time constant to stimulate a restoration of more normal epidermal and dermal architecture in the region of a stretch mark. The method of application will depend on the site of the stretch mark, as well as on the width of the defect being treated.

The present invention provides a cosmetic method for regenerating the skin in the region of a stretch mark, the method comprising operating a source of thermal energy with a low thermal time constant and directing it at the surface of the skin adjacent to and within a stretch mark, forming first and second adjacent regions of thermally-modified tissue, the first region being adjacent to, and overlying, the second region, and the first reason being thermally modified to a greater extent than the second region such that, following treatment, the width of the stretch mark is reduced and the reticular architecture of the dermis in the stretch mark is at least partially restored.

In a preferred embodiment, the source of thermal energy is such that the junction of the first and second regions lies at, or superficial to, the dermo-epidermal junction, such that the use of repetitive treatments repetitively reduces the width of the stretch mark, the reticular architecture of the dermis in the stretch mark being at least partially restored during each treatment.

Preferably, the thermal energy source is operated so that a line of cleavage occurs within the skin following treatment, the line of cleavage occurring between the first and second regions.

In this case, the tissue below the line of cleavage in the second region may include the lower epidermis, the basal membrane and the dermo-epidermal junction. Advantageously, at least the thermally modified basal membrane and the dermo-epidermal junction are regenerated.

Preferably, the tissue below the line of cleavage includes at least a portion of the papillary and the reticular dermis, and the epidermis, the dermo-epidermal junction and at least a portion of the papillary dermis are sloughed and regrown from cells derived from hair follicles within the region of the thermal treatment.

The depth of the line of cleavage will also depend on the thickness of the skin in the region of the stretch mark for a given amount of energy delivered by the thermal energy source. Skin on the front, ventral surface of the body is typically thinner than that on the back, dorsal surface of the body, so that the energy used on the front surface is typically one half to two thirds of that used on the back to produce a similar depth at which the line of cleavage forms.

The use of a topical anaesthetic will also influence the depth at which the line of cleavage forms such that, when no topical anaesthesia is used, the energy is typically reduced by one third, to produce a similar depth at which the line of cleavage forms compared to that when a topical anaesthetic is used. The influence of the use of a topical anaesthetic on the depth at which a line of cleavage is formed is described in greater detail in the specification of our International Patent Application No. PCT/GB2006/000556.

Conveniently, the thermal energy source operates on the surface of the skin via an optical target marking projector which defines a treatment area on the surface of the skin.

Preferably, the target marker is positioned along the edge of the stretch mark so that the treatment area is adjacent to and within the stretch mark, and following the direction of thermal energy onto the skin surface with the target marking projector in said first position, the target marking projector is moved along the edge of the stretch mark so that the area of skin surface provided with a visible target marker overlaps the area previously treated, and the process is continued until treatment has been carried out along the entire edge of the stretch mark.

In a preferred embodiment, the method further comprises applying adhesive strips to the edges of the stretch mark following treatment to approximate the dermal collagen at the edges of the stretch mark.

Preferably, the method further comprises applying adhesive strips to the edges of the stretch mark following treatment to remove at least some tension from the treated area during the healing process.

Advantageously, the method further comprises the application of collagenous fillers or fibroblasts prior to the operation of the source of thermal energy. In this case, the collagenous fibres or fibroblasts are derived from the patient being treated, from animal sources, or from human sources involving allogenic cell culture.

The invention also provides a cosmetic method for regenerating the skin in the region of a stretch mark, the method comprising the selection of a thermal energy level produced by a plasma formed in a diatomic gas such that the level of thermal energy produces first and second regions of thermal modification, the first region being thermally modified to a greater extent than the second region, wherein the selection of the thermal energy level defines the depth from the skin surface where the junction of the first and second regions will occur.

Preferably, the depth of the junction between the first and second regions forms superficial to the dermo-epidermal junction, or below the dermo-epidermal junction.

Advantageously, the depth of the junction between the first and second regions is selected according to the width of the stretch mark, or according to the pigmentary changes present in the stretch mark.

Conveniently, the depth of the junction between the first and second regions is selected for progressively reducing the width of the stretch mark, using repeat treatments without sloughing of the dermo-epidermal junction, followed by a final treatment whereby the depth of the junction between the first and second regions is deeper than the dermo-epidermal junction.

In yet another embodiment, the method comprises selecting a level of thermal energy such that the junction of the first and second regions lies below the dermo-epidermal junction, whereby the epidermis, the DEJ and at least a portion of the papillary dermis sloughs during the healing phase. This aspect of the method may be applied of the defect of the stretch mark is less than the diameter of the thermal effect produced with a single pulse, or following a series of treatments for progressively remodelling the stretch mark, but where the skin surface is still irregular, exhibits a persistent atrophic appearance, or in which the pigmentary changes have not been sufficiently corrected. This embodiment of the method beneficially restores a new epidermis without the translucency and atrophic appearance associated with stretch marks. A further benefit will be that any increased pigmentation at the DEJ will also be eliminated.

The invention will now be described in greater detail, by way of example, with reference to the drawings, in which:

FIG. 4 is a diagram showing an optical target marking projector of the system of FIG. 1;

FIG. 10 is a schematic representation of a stretch mark;

FIG. 11 is a section taken on the line A-A of FIG. 10;

FIG. 14 is a schematic representation of a stretch mark following cosmetic treatment in accordance with the invention; and FIG. 15 is a cross-section taken on the line C-C of FIG. 14.

Figure 1:
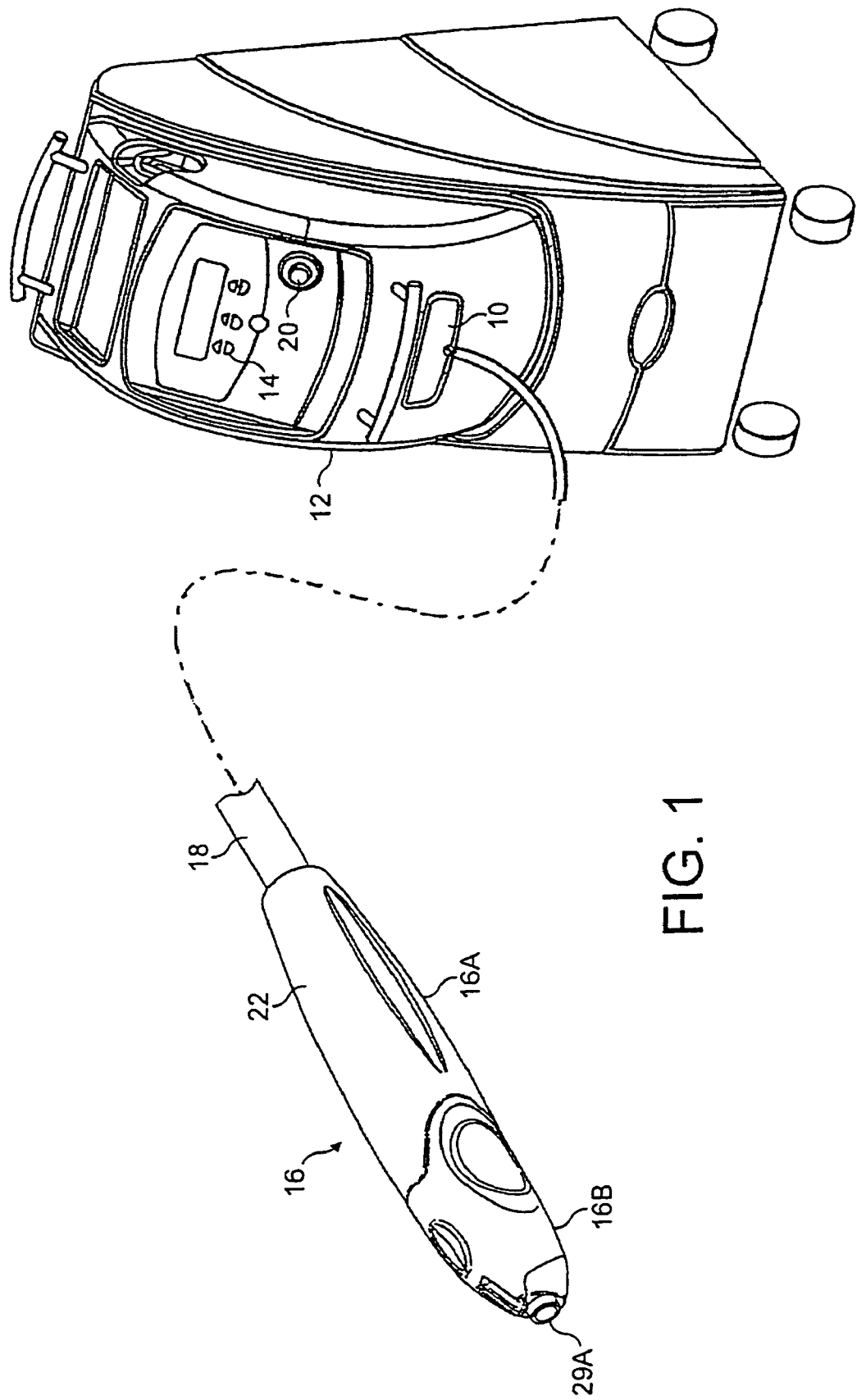
FIG. 1 is a diagrammatic view of a tissue treatment system constructed in accordance with the invention.

Referring to the drawings, FIG. 1 shows a tissue treatment system having a treatment power source in the form of an r.f. generator 10 mounted in a floor-standing generator housing 12, and having a user interface 14 for setting the generator to different energy level settings. A handheld tissue treatment instrument 16 is connected to the generator 10 by means of a cord 18. The instrument 16 comprises a handpiece having a re-usable handpiece body 16A and a disposable nose assembly 16B.

The generator housing 12 has an instrument holder 20 for storing the instrument 16 when not in use.

Figure 2:
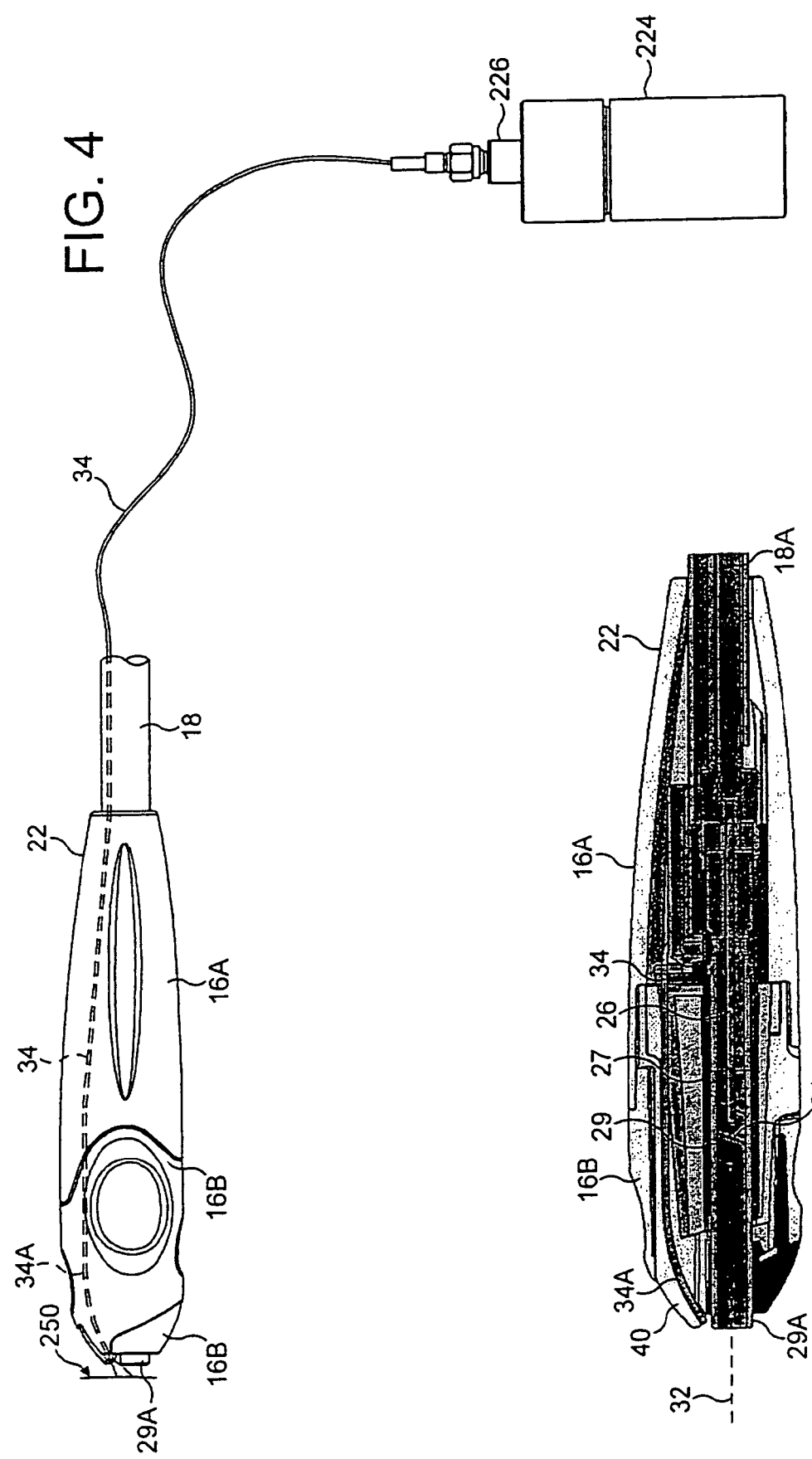
FIG. 2 is a longitudinal cross-section of a tissue treatment instrument forming part of the system of FIG. 1.

The cord 18 is provided with a coaxial cable 18A (see FIG. 2) for conveying r.f. energy from the generator 10 to the instrument 16, and a gas supply pipe (not shown) for supplying nitrogen gas from a gas reservoir or source (not shown) inside the generator housing 12. The cord 18 also contains an optical fibre light guide 34 (see FIG. 4) for transmitting visible light to the instrument 16 from a light source (not shown) in the generator housing 12. At its distal end, the cord 18 passes into a casing 22 of the re-usable handpiece body 16A The coaxial cable 18A is connected to inner and outer electrodes 26 and 27 within the re-usable handpiece body 16A, as shown in FIG. 2. The inner electrode 26 extends longitudinally within the outer electrode 27, a heat-resistant tube 29 (preferably made of quartz) housed in the disposable instrument nose assembly 16B extending between the two electrodes. When the nose assembly 16B is secured to the handpiece body 16A, the interior of the tube 29 is in communication with the gas supply pipe interior, the nose assembly being received within the handpiece body such that the inner electrode 26 extends axially into the tube, and the outer electrode 27 extends around the outside of the tube.

A resonator, in the form of a helically-wound tungsten coil 31, is located within the tube 29, the coil being positioned such that, when the disposable nose assembly 16B is secured in position on the handpiece body 16A, the proximal end of the coil is adjacent to the distal end of the inner electrode 26. The coil 31 is wound such that it is adjacent to, and in intimate contact with, the inner surface of the tube 29.

In use of the instrument 16, nitrogen gas is fed by the supply pipe to the interior of the tube 29 where it reaches a location adjacent to the distal end of the inner electrode 26. When an r.f voltage is supplied via the coaxial cable 18A to the electrodes 26 and 27, an intense r.f. electric field is created inside the tube 29 in the region of the distal end of the inner electrode. The field strength is aided by the helical coil 31 which is resonant at the operating frequency of the generator 10 and, in this way, conversion of the nitrogen gas into a plasma is promoted, the plasma exiting as a jet at a nozzle 29A of the tube 29. The plasma jet, centred on a treatment beam axis 32 (this axis being the axis of the tube 29), is directed onto tissue to be treated, the nozzle 29A typically being held a few millimeters from the surface of the tissue.

The handpiece 16 also contains the end of the optical fibre light guide 34 which extends through the cord 18 into the handpiece where its distal end portion 34A is bent inwardly towards the treatment axis 32 to terminate at a distal end which defines an exit aperture adjacent to the nozzle 29A. The inclination of the fibre guide 34 at this point defines a projection axis for projecting a target marker onto the tissue surface, as will be described in more detail below.

Following repeated use of the instrument, the tube 29 and its resonant coil 31 require replacement. The disposable nose assembly 16B containing these elements is easily attached and detached from the re-usable handpiece body 16A of the instrument 16, the interface between the two components 16A, 16B of the instrument providing accurate location of the tube 29 and the coil 31 with respect to the electrodes 26, 27.

Figure 3:
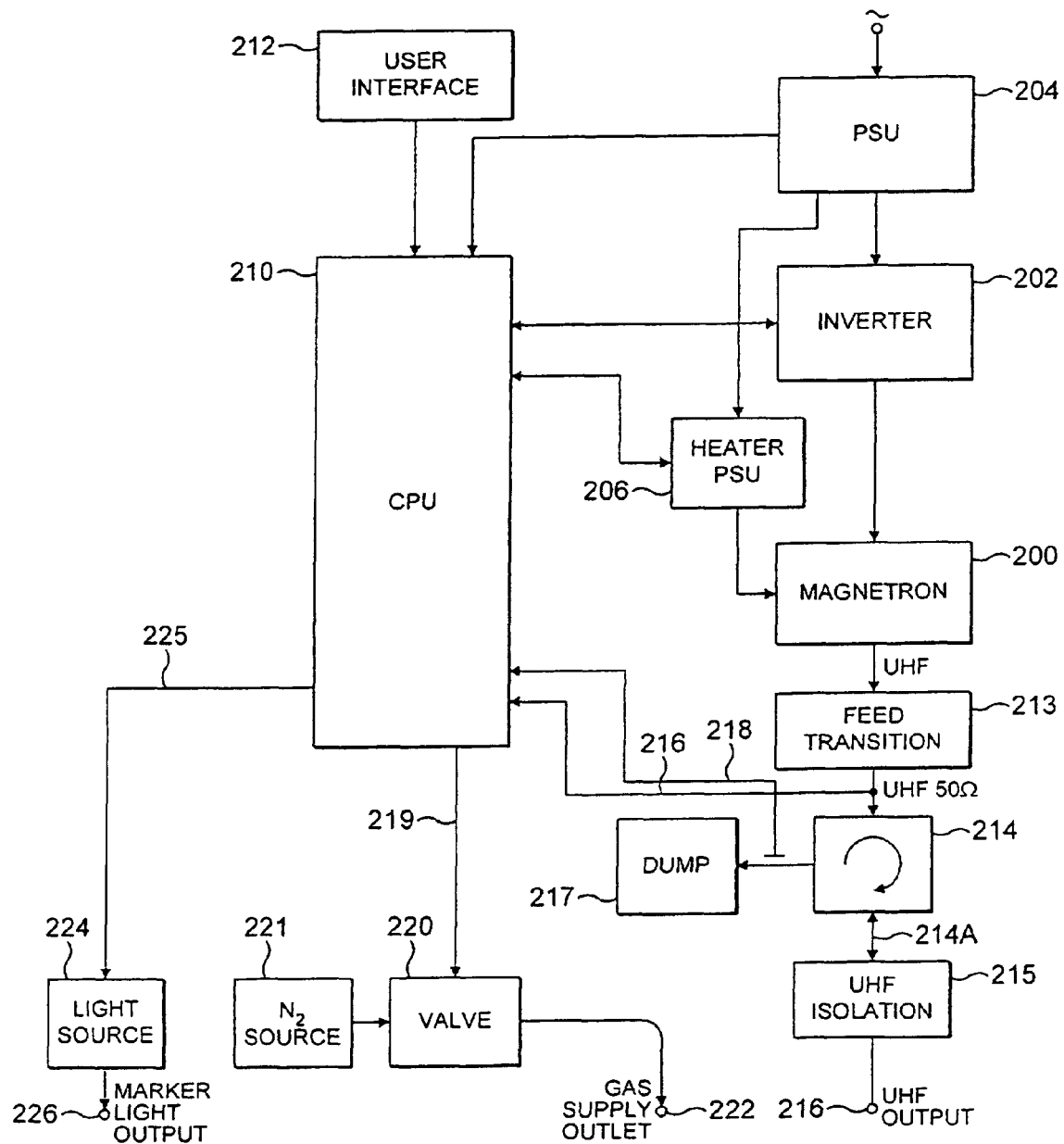
FIG. 3 is a block diagram of a radio frequency generator for use in the system of FIG. 1.

Referring to FIG. 3, r.f. energy is generated in a magnetron 200. Power for the magnetron 200 is supplied in two ways, firstly as a high DC voltage for the cathode, generated by an inverter 202 supplied from a power supply unit 204 and, secondly, as a filament supply for the cathode heater from a heater power supply unit 206. Both the high voltage supply (represented by the inverter 202) and the filament supply 206 are coupled to a CPU controller 210 for controlling the power output of the magnetron 200. A user interface 212 is coupled to the controller 210 for the purpose of setting the power output mode, amongst other functions.

The magnetron 200 operates in the high UHF band, typically at 2.475 GHz, producing an output on an output line which feeds a feed transition stage 213 for converting the magnetron output to a coaxial 50 ohms feeder, low frequency AC isolation also being provided by this stage. Thereafter, a circulator 214 provides a constant 50 ohms load impedance for the output of the feed transition stage 213. Apart from a first port coupled to the transition stage 213, the circulator 214 has a second port 214A coupled to a UHF isolation stage 215 and hence to the output terminal 216 of the generator 10 for delivering RF power to the handheld instrument 16 (FIG. 1). Reflected power is fed from the circulator 214 to a resistive power dump 215. Forward and reflected power sensing connections 216 and 218 provide sensing signals for the controller 210.

The controller 210 also applies, via a line 219, a control signal for opening and closing a gas supply valve 220 so that nitrogen gas is supplied from a source 221 to a gas supply outlet 222, from where it is fed through the gas supply pipe in the cord 18 to the instrument 16 (FIG. 1), when required. A light source 224, forming part of the above-mentioned optical target marker projector, is connected to the controller 210 by a control line 225, and produces a target marker light beam at an optical marker light output 226.

The controller 210 is programmed to pulse the magnetron 200 so that, when the user presses a footswitch (not shown in the drawings), r.f. energy is delivered as a pulsed waveform to the UHF output 216, typically at a pulse repetition rate of between about 1 Hz and about 4 Hz. A single pulse mode is also provided. The controller 210 also operates the valve 220, so that nitrogen gas is supplied to the handheld instrument simultaneously with the supply of r.f. energy. The light source 224 can be actuated independently of r.f. energy and nitrogen gas supply. Further details of the modes of delivery of r.f. energy are set out in the above-mentioned U.S. Pat. No. 6,723,091.

The optical fibre light guide 34 and the light source 224 form part of an optical target marker projector which is shown as a whole in FIG. 4. The light source 224 is in the generator housing 12 (see FIG. 1) and, coupled to its optical output 226, is the optical fibre line 34 which passes through the cord 18 connecting the handpiece 16 to the generator housing 12 and, thence, into the casing 22 of the handpiece. Within the handpiece, the fibre guide 34 extends generally parallel to, and offset from, the treatment beam axis 32 until it reaches a distal end portion of the handpiece. There, the distal end portion 34A of the fibre guide 34 is bent towards the treatment beam axis 32, as shown. The distal end of the fibre guide 34 forms an exit aperture for the guided marker beam which, when the light source 224 is activated, is projected as a diverging beam onto the tissue surface 250 to be treated.

Figure 5:
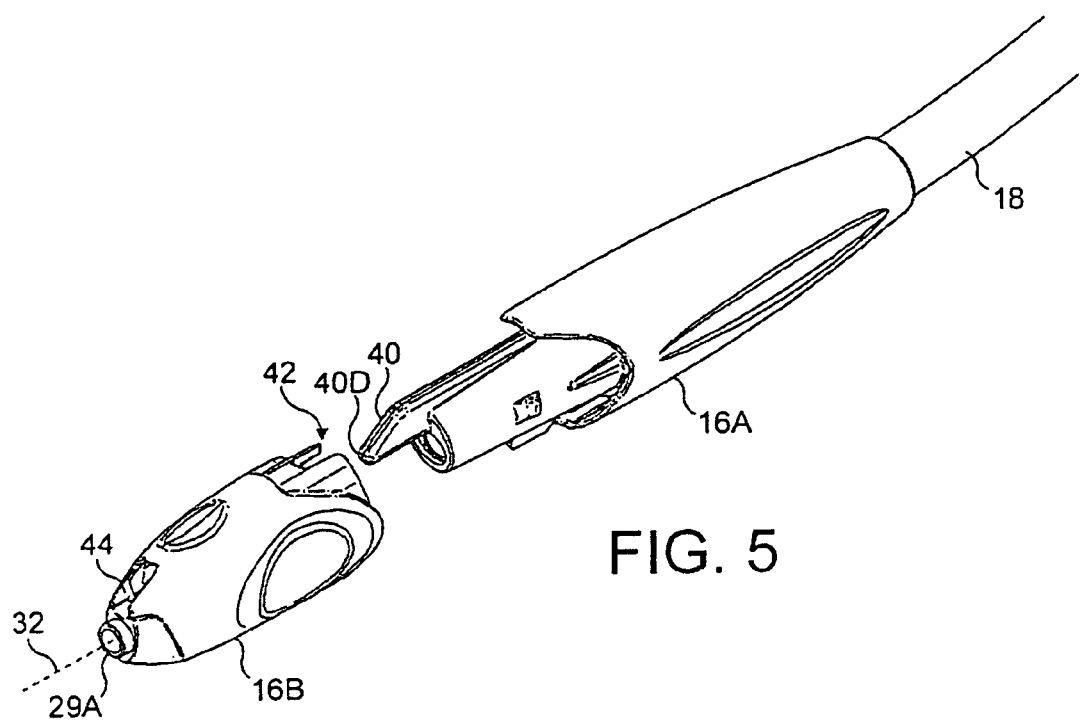
FIG. 5 is an exploded perspective view of the tissue treatment instrument shown in FIG. 2.

The distal end portion 34A of the optical fibre guide 34 is supported within the disposable nose assembly 16B by an elongate rigid fibre guide support 40, as shown in the exploded view of the handpiece appearing in FIG. 5. When the disposable nose assembly 16B is fitted to the handpiece body 16A, the fibre guide support 40 extends through a passage 42 in the handpiece body 16A, and is exposed at an aperture 44 of the nose assembly 16B so that the distal end of the fibre guide 34, which is at the distal end 40D of the support, lies adjacent to the plasma nozzle 29A. The passage 42 in the disposable nose assembly 16B locates the fibre guide support 40 and, therefore, the distal end portion 34A of the fibre guide, aligning the guide so that it is correctly positioned with respect to the plasma nozzle 29A and the treatment beam axis 32.

Figure 6:
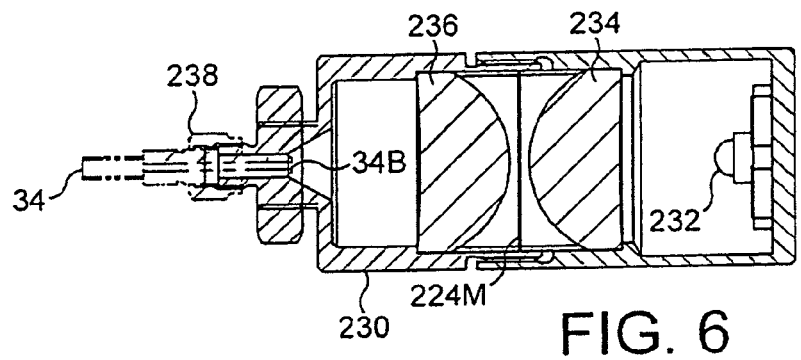
FIG. 6 is a cross-section of a light source forming part of the target marking projector of FIG. 4.

Referring to FIG. 6, the light source 224 comprises an illuminated mask 224M mounted transversely in an elongate light source housing 230. The mask 224M is illuminated by a light emitting diode 232 mounted at one end of the housing 230, visible light from the LED 232 passing through a first collimator lens 234, then through the mask 224M, following which it is concentrated by a second lens 236 onto the proximal end 34B of the fibre guide 34 for transmission to the handpiece 16 shown in FIG. 4. The fibre guide 34 is removable from the light source housing 230 by releasing an optical fibre connector 238.

The LED 232 is chosen to produce a blue light, since this colour has the advantage of being easily seen on a range of skin colours from light to dark. Other colours may, of course, be used. A laser diode light source may also be used.

Figure 7:
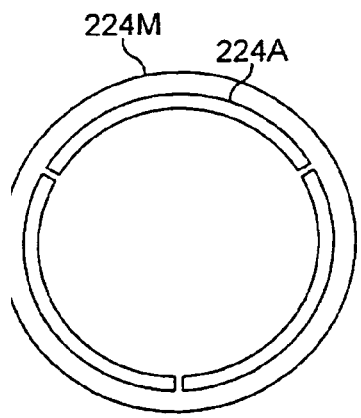
FIG. 7 is an axial view of a light source mask.
Figure 8:
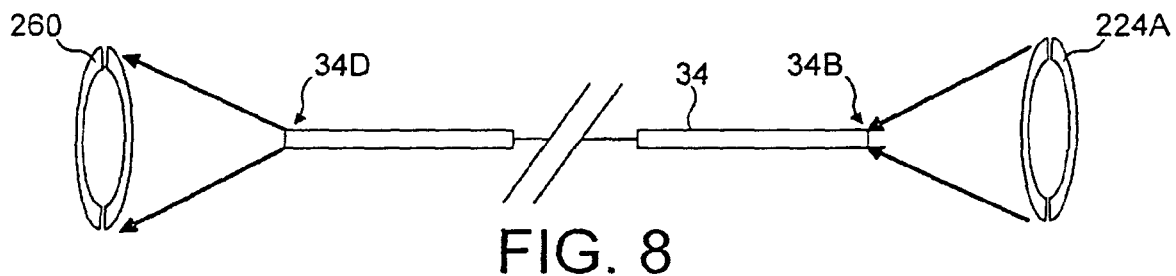
FIG. 8 is a diagram showing the principle of the transmission of a target marker image in an optical fibre.

Referring to FIG. 7, the light source mask 224M, when viewed in the axial direction of the light source housing 230, is seen to have an annular aperture 224A. It is this aperture 224A which, when illuminated by the LED 232, is imaged on the tissue surface to be treated, albeit with some distortion in the optical fibre guide 34. It is a property of a straight optical fibre with end faces perpendicular to its axis that, when light is incident on one of the ends at a given angle to the axis, the light emitted from the other end is emitted at the same angle, providing the angle of incidence is no greater than the so-called "acceptance angle" associated with the material of the fibre. The acceptance angle is $\sin^{-1}$ (NA) where NA is the numerical aperture of the fibre. This property of optical fibres, insofar as it relates to the present invention is illustrated in FIG. 8. The light from the light source, shown as the illuminated aperture 224A in FIG. 8, is focused onto the proximal end 34B of the fibre guide 34, the angle of the edge of the annulus with respect to the fibre axis being less than the acceptance angle for the material of the fibre. At the distal end 34D, light transmitted from the proximal end 34B emerges, as shown, at the same angle with respect to the fibre axis as the incident light at the proximal end, the emerging light then diverging so that an image 260 of the annulus is formed in a plane spaced from the guide distal end 34D. As stated above, light from the light source aperture 224A is concentrated on the guide proximal end 34B by the second lens 236 in the light source housing as described above with reference to FIG. 6. In practice, the focal length of the lens 236 is arranged to be greater than the spacing between the lens and the fibre proximal end 34B, so that the image of the aperture 224A is spaced beyond the distal end of the fibre guide, as shown in FIG. 8.

Multiple internal reflections, the length of the fibre, and bending of the fibre, amongst other effects, tend to spread the incident rays to some degree. The mask 224M is located in a collimated beam of light produced between the two lenses 234, 236 of the light source. Accordingly, with an annular aperture 224A, a cylindrical annulus of light is incident upon the second lens 236. The image of the annulus is transmitted through the fibre guide 34 with a fidelity dependent on the quality of the fibre, its length, and its degree of bending. A low cost polymer fibre may be used. The best results, however, are obtained with a silica fibre, which has lower losses and distortion. Polymer fibres typically have a numerical aperture in the range of from 0.3 to 0.75, while silica fibres have a numerical aperture generally within the range 0.12 to 0.48.

Figure 9:
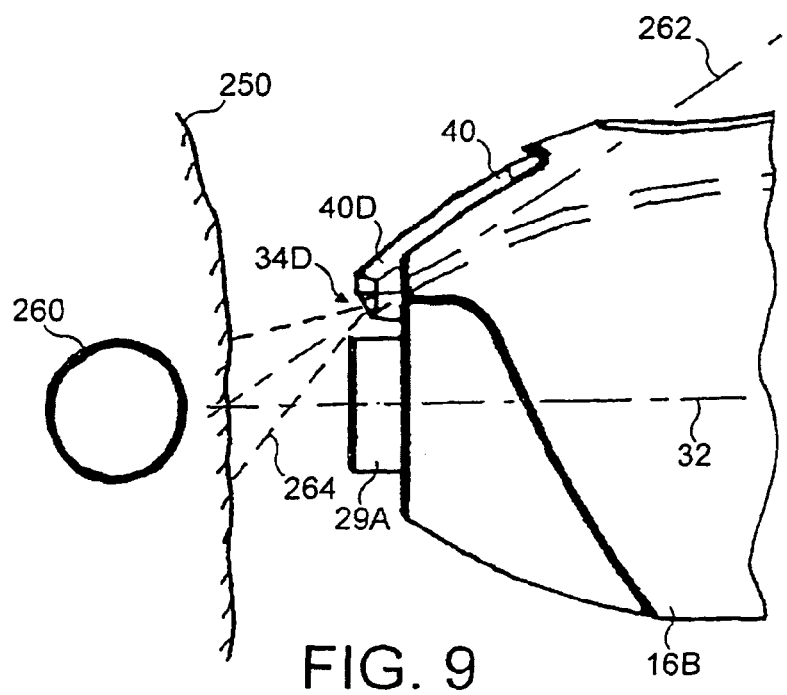
FIG. 9 is a detail from FIG. 4 showing the distal end of the treatment instrument and the projection of the marker image onto a tissue surface.

The projection of the annular image 260 onto a target tissue surface will now be described with reference to FIG. 9. In its support 40, the distal portion 34A of the fibre guide 34 is bent towards the treatment beam axis 32 so that, at the exit aperture formed by the distal end 34D of the fibre guide, light transmitted through the fibre guide emerges centred in an inclined projection axis 262 which intersects the treatment beam axis 32 at a predetermined spacing from the plasma exit nozzle 29A. The properties of the second lens 236 in the light source housing 230 and of the fibre guide 34 are such that the focused image 260 of the light source annulus 224A appears approximately in a perpendicular plane passing through the intersection of the two axes 32, 262. The degree of divergence of the projected marker beam 264 is such that, at the projection plane, the size of the image marker 260 is approximately the same as the external diameter of the plasma exit nozzle 29A. The predetermined spacing which is determined by the configuration of the projector, corresponds to the preferred spacing of the tissue surface 250 from the end of the plasma exit nozzle 29A for optimum clinical effect. Accordingly, in use, the correct spacing of the handpiece 16 from the tissue surface 250 can be judged by the user by locating the handpiece so as to produce an image of a required size with reference to the diameter of the exit nozzle 29A. In other words, the size of the marker image 260 indicates the stand-off distance of the handpiece 16 from the tissue surface 250 as a result of the conical nature of the projected beam, the axis of the cone being approximately coincident with the exit aperture of the fibre guide 34. In this embodiment, the handpiece 16 is correctly spaced from the tissue surface 250 when the diameter of the marker is approximately the same as the external diameter of the nozzle 29A. The area occupied by the marker 260 also indicates, at least approximately, the area of clinical effect, dependent on the size of the nozzle 29A.

Large deviations of the treatment beam axis 32 from the preferred perpendicular orientation with respect to the tissue surface 250 are indicated by a pronounced elliptical image (as opposed to a circular or near-circular image).

By actuating the light source 224 before treatment begins, the user can position the handpiece 16 at the required spacing from the tissue surface 250, and can identify the area of clinical effect before the gas plasma is actuated.

Variations to the system include the following.

With appropriate modification to the mask 224M of the light source 224, a solid circle of light may be projected on the tissue surface rather than an annulus.

In the preferred embodiment, the exit aperture formed by the distal end 34D of the fibre guide 34 is radially offset with respect to the treatment beam axis, the distal end portion 34A of the fibre guide being bent to project the annulus of light such that the centre of the projected annulus is centrally positioned with respect to the centre of the zone of treatment produced by a gas plasma jet from the nozzle 29A. Alternatively, the distal face of the fibre 34 may be processed such that it is not perpendicular to the fibre axis. In this case, the light is projected at an angle with respect to the fibre axis at its exit aperture and may, thereby, be used to modify the shape of the image and its spacing from the nozzle 29A.

In another embodiment, at least one additional fibre guide may be employed between the light source 224 and the distal end of the handpiece 16. For example, part of the marker image may be transmitted by one fibre guide and another part of the image by another fibre guide. In particular, half of the image may be projected by a fibre guide offset on one side of the plasma exit nozzle 29A, and the other half of the image may be projected by a fibre guide terminating on the diametrically opposite side of the nozzle, the respective projection axes intersecting at the required tissue treatment spacing from the nozzle. In this way, the image appears disjointed or misshapen at spacings of the instrument greater or less than the optimum spacing.

In yet a further alternative of the embodiment, the tube 29 itself may be used as a light guide for projecting the marker.

It is possible to mount the projector completely within the handset, powering the light source from a battery.

Systems according to the invention deliver heating energy to the tissue from a source having a low thermal time constant. Typically, treatment energy can be delivered in pulses of very short duration (typically 0.5 to 100 ms), and without reliance on an intermediary conversion from one kind of energy to another such as a chromophore in laser energy and tissue resistivity in radio frequency energy.

Figure 13:
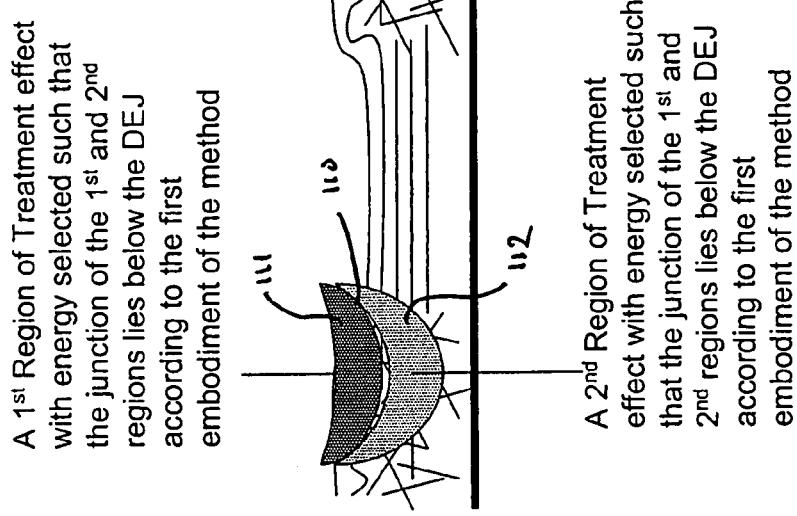
FIG. 13 is a cross-section taken on the line B-B of FIG. 12.

In use, the instrument 16 is passed over the surface 250 of tissue to be cosmetically treated, with the nozzle 29a typically being held a few millimeters from the surface of the tissue. The pulse duration and energy levels are chosen so as to form first and second adjacent regions 111 and 112 (see FIG. 13) of thermally-modified tissue in the region of the DE Junction. The first, upper region 111 is termed a zone of thermal damage, having a thermal modification which is greater than that of the second, lower region 112. The thermally-damaged zone 111 is thermally modified to an extent that it separates from the second region 112 some days after the delivery of the thermal energy. Following separation of the first damaged region, the epidermis and the upper region of the dermis regenerate naturally.

FIGS. 10 and 11 show a stretch mark indicated generally by the reference numeral 101. The edges of the stretch mark 101 are shown at 102, the cross hatching 103 indicates regions where collagen is disrupted, and the shaded area 104 is indicative of the appearance of subcutaneous tissue. FIG. 11 also shows the dermis 105 and the epidermis 106, together with the normal reticular matrix of collagen and elastin 107 outside the stretch mark 101, and the planar unipolar orientation 108 in the base of the stretch mark 101.

Figure 12:
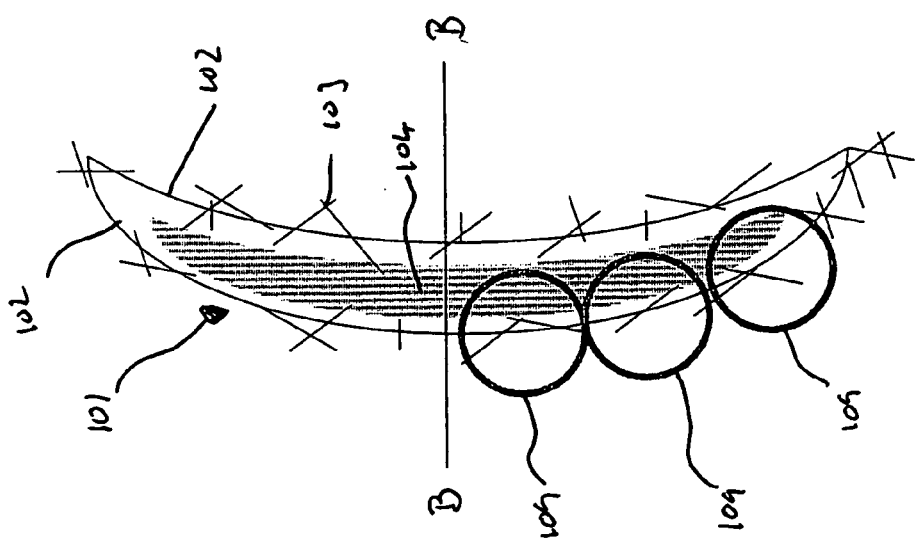
FIG. 12 is a view similar to that of FIG. 10, but showing how successive pulses of treatment are carried out.

The stretch mark 101 is relatively small, having a width which is substantially equal to the diameter of the zone of effect induced by a pulse emitted by the instrument 16. In this case, treatment can be carried out using a single, high energy pulse selected to form the first and second adjacent regions referred to above. As shown in FIG. 12, treatment is carried out by applying successive single pulses, indicated by the reference numerals 109 along the edges 102 of the stretch mark 101. As described in greater detail in the specification of U.S. patent application Ser. No. 11/281,594, a line of cleavage 110 develops between the two regions 111 and 112 of thermally-modified tissue formed by the pulses between two and five days after treatment (see FIG. 13). This line of cleavage 110 forms at least below the DEJ. Alternatively, the thermal energy level of the instrument can be modified so that the line of cleavage 110 developed between the regions 111 and 112 is superficial to the DEJ. The pulses are laid down using the target marker described above so that the rings are substantially adjacent, but have an overlap of 15 to 20%, with the centres of the ring being positioned along the edges 102 of the stretch mark 101. This results in half the treatment zone lying within the stretch mark 101, and half lying over the adjacent normal skin. This treatment results in the denaturation of the collagen which, in turn, results in shrinkage such that the stretch mark 101 will partially close by approximately 10 to 15% of its width, as shown in FIG. 14 by the reference numeral 113.

FIG. 15 shows the position ten days after treatment of the stretch mark 101 with a pulse energy of between 1.5 and 3.5 Joules depending upon the thickness of the skin in the region of the stretch mark, and the selection of the anaesthetic method used. Here the epidermis has been fully regenerated over the stretch mark, as indicated by the reference numeral 114, with residual activity in the basal layer, and the zone of thermal modification is now apparent, as intense fibroblast activity has regenerated the reticular matrix of collagen and elastin in the region on the stretch mark, as indicated by the reference numeral 115. Thus, the matrix orientation of dermal collagen is restored as part of the healing process, and this is particularly advantageous in correcting the linear orientation of collagen fibres associated with the stretch mark 101, and restoring, in at least part, the elastic properties of the damaged skin. The healing process will blend across the edges of the stretch mark 101 into the normal skin, and the cross-hatched appearance of the edges of the stretch mark are lost.

The tissue below the line of cleavage 110 in the region 112 includes the lower epidermis, the basal membrane and the DEJ. The treatment is such that at least the thermally-modified basal membrane and the DEJ are regenerated.

The tissue below the line of cleavage 110 may include at least a portion of the capillary and the reticular dermis, in which case the epidermis, the DEJ and at least a portion of the papillary dermis are sloughed and re-grown from cells derived from hair folicals within the region of the thermal treatment.

Where the width of a stretch mark exceeds the width of the zone of effect produced by the plasma pulses emitted by the instrument 16, the treatment method is modified to provide multiple steps in order progressively to shrink the size of the stretch mark. The pulse energy selected should be such as to create denaturation of dermal collagen, whilst preserving as much of the epidermis as possible.

As with the treatment described above with reference to FIGS. 10 to 15, the pulses of energy are applied along the edges of the stretch mark. This results in a shrinkage such that the stretch mark will partially close by approximately 10 to 15 percent of its width. A second treatment step is then carried out along the new edges of the stretch mark, and further treatment steps are carried out repeatedly until the stretch mark is reduced sufficiently in size that a further treatment step similar to that described above with reference to FIGS. 10 to 15 may be applied to remove any elasticity or pigmentary change in the epidermis. For each successive treatment step, the pulses are laid down using the target marker by moving the target marker towards the centre of the stretch mark by an amount equal to the radius of the target ring.

During the healing process, following denaturation of collagen, the regenerating collagen is effectively "sticky", such that, if two areas are brought into proximity with one another, the collagen fibres will interdigitate to form a matrix across the gap, as indicated by the reference numeral 116 in FIG. 15.

The thermal energy level of the instrument 16 can be selected to define the depth from the skin surface where the junction between the first and second regions 111 and 112 occurs. Thus, the depth of this junction can be arranged to form superficial to the DEJ or below the DEJ. The depth of the junction between the two regions 111 and 112 can also be selected according to the width of the stretch mark 101, or according to the pigmentary changes present in the stretch mark. Moreover, the depth of the junction between the regions 111 and 112 can be selected for progressively reducing the width of the stretch mark 101, using repeat treatments without sloughing of the DEJ, followed by a final treatment whereby the depth of the junction is deeper than the DEJ.

A benefit of using a diatomic plasma is that it is able to deliver a relatively large amount of energy which causes heating in a short period of time. This enables delivery in discreet pulses of millisecond duration, and is in contrast to heat conduction from a merely hot gas. In the preferred embodiment, energy from 1 Joule to 4 Joules is delivered in a period of 4.5 to 15.4 milliseconds respectively for a nozzle with an exit diameter of 5 millimeters, and delivers from less than 0.5 Joules up to 2 Joules in the same period for a nozzle 29A with an exit diameter of less than 1.5 millimeters. Experiments have shown that useful clinical effects are achieved with yet longer pulses extending to 50 milliseconds, and further analysis shows extension up to 100 milliseconds or more will provide useful effects. In addition, the pulse width may be shortened to deliver the same, or otherwise similar, useful heating energy. Plasma pulses as short as 0.5 milliseconds have been produced with the system described above.

Another benefit is that oxygen is purged from the skin surface by the plasma and the flow of inert gas that follows immediately following a plasma pulse. As a result, the oxidative carbonisation that often occurs at the skin surface on application of thermal energy is avoided, leaving a desiccated intact epithelium with minor structural alteration.

This minor structural alteration is nonetheless important in providing yet another benefit of the invention, as it changes the thermal characteristics of the epidermis at higher energy settings. Following a single pass of plasma over the skin surface at an energy setting greater than 2 Joules, the epidermal cells at the basal membrane are heated to a degree that produces vacuolation of the cellular contents. This produces a natural insulator limiting the absorption and depth of penetration of energy from subsequent passes. This is a beneficial safety feature that avoids the risk of excessive damage by inadvertent application of multiple passes to the same site on the skin surface.

The reason for using a diatomic plasma which delivers a relatively large amount of energy in a short period of time is that the irreversible clinical effects (the thermal modification and thermal damage of the tissue) occur over tissue depths that result in the desired clinical effects, whilst avoiding any undesired clinical effects. If the heating energy is delivered over too long a time, the effects of convection from the skins surface and conduction into the underlying tissue will be such that no significant temperature rise results. On the other hand, if the time is too short, then irreversible effects (such as water vaporising) at or near the skins surface will carry away otherwise useful heating energy.

It will be apparent that modifications could be made to the method described above. For example, the method could be modified by applying adhesive strips to the edges of the stretch mark following treatment to approximate the dermal collagen at the edges of the stretch mark. Alternatively, the adhesive strips could be applied to the edges of the stretch mark following treatment to remove at least some of the tension from the treated area during the healing process. It would also be possible to modify the method by the application of collagenous fillers of fibroblasts prior to the operation of the source of thermal energy. In this case, the collagenous fillers or fibroblasts could be derived from the patient being treated, from animal sources, or from human sources which involve hallogenic cell culture.

The invention claimed is:

1. A cosmetic method of regenerating the skin in the region of a stretch mark, the method comprising operating a source of thermal energy with a low thermal time constant and directing it at the surface of the skin adjacent to and within a stretch mark, forming first and second adjacent regions of thermally-modified tissue, the first region being adjacent to, and overlying, the second region, and the first region being thermally modified to a greater extent than the second region such that, following treatment, the width of the stretch mark is reduced and the reticular architecture of the dermis in the stretch mark is at least partially restored.

2. A method as claimed in claim 1, wherein the source of thermal energy is such that the junction of the first and second regions lies at, or superficial to, the dermo-epidermal junction, such that the use of repetitive treatments repetitively reduces the width of the stretch mark, the reticular architecture of the dermis in the stretch mark being at least partially restored during each treatment.

3. A method as claimed in claim 1, wherein the source of thermal energy is such that the junction of the first and second regions lies at least below the dermo-epidermal junction, such that the use of repetitive treatments repetitively reduces the width of the stretch mark, the reticular architecture of the dermis in the stretch mark being at least partially restored during each treatment.

4. A method as claimed in claim 3, wherein the thermal energy source is operated so that a line of cleavage occurs within the skin following treatment, the line of cleavage occurring between the first and second regions.

5. A method as claimed in claim 4, wherein the tissue below the line of cleavage in the second region includes the lower epidermis, the basal membrane and the dermo-epidermal junction.

6. A method as claimed in claim 5, wherein at least the thermally modified basal membrane and the dermo-epidermal junction are regenerated.

7. A method as claimed in claim 4, wherein the tissue below the line of cleavage includes at least a portion of the papillary and the reticular dermis.

8. A method as claimed in claim 7, wherein the epidermis, the dermo-epidermal junction and at least a portion of the papillary dermis are sloughed and regrown from cells derived from hair follicles within the region of the thermal treatment.

9. A method as claimed in claim 8, wherein the thermal energy source operates on the surface of the skin via an optical target marking projector which defines a treatment area on the surface of the skin.

10. A method as claimed in claim 9, wherein the target marker is positioned along the edge of the stretch mark so that the treatment area is adjacent to and within the stretch mark, and following the direction of thermal energy onto the skin surface with the target marking projector in said first position, the target marking projector is moved along the edge of the stretch mark so that the area of skin surface provided with a visible target marker overlaps the area previously treated, and the process is continued until treatment has been carried out along the entire edge of the stretch mark.

11. A method as claimed in claim 10, further comprising applying adhesive strips to the edges of the stretch mark following treatment to approximate the dermal collagen at the edges of the stretch mark.

12. A method as claimed in claim 10, further comprising applying adhesive strips to the edges of the stretch mark following treatment to remove at least some tension from the treated area during the healing process.

13. A method as claimed in claim 12, further comprising the application of collagenous fillers or fibroblasts prior to the operation of the source of thermal energy.

14. A method as claimed in claim 13, wherein the collagenous fillers or fibroblasts are derived from the patient being treated.

15. A method as claimed in claim 13, wherein the collagenous fillers or fibroblasts are derived from animal sources.

16. A method as claimed in claim 3, wherein the collagenous fillers or fibroblasts are derived from human sources and involve allogenic cell culture.

\* \* \* \* \*